United States Patent
Kadyrov

(10) Patent No.: US 10,781,164 B2
(45) Date of Patent: Sep. 22, 2020

(54) REDUCTIVE ALKYLATION OF AMINES WITH ORTHOCARBOXYLIC ACID ESTERS

(71) Applicant: Evonik Degussa GmbH, Essen (DE)

(72) Inventor: Renat Kadyrov, Frankfurt (DE)

(73) Assignee: Evonik Operations GmbH, Essen (DE)

( * ) Notice: Subject to any disclaimer, the term of this patent is extended or adjusted under 35 U.S.C. 154(b) by 230 days.

(21) Appl. No.: 16/074,306

(22) PCT Filed: Jan. 23, 2017

(86) PCT No.: PCT/EP2017/051313
§ 371 (c)(1),
(2) Date: Jul. 31, 2018

(87) PCT Pub. No.: WO2017/133913
PCT Pub. Date: Aug. 10, 2017

(65) Prior Publication Data
US 2020/0231537 A1    Jul. 23, 2020

(30) Foreign Application Priority Data
Feb. 3, 2016   (EP) .................................... 16154092

(51) Int. Cl.
*C07C 227/18* (2006.01)
*C07D 265/30* (2006.01)
*C07D 207/06* (2006.01)
*C07D 211/16* (2006.01)
*C07C 209/26* (2006.01)
*C07C 229/24* (2006.01)
*C07C 211/48* (2006.01)
*C07C 229/36* (2006.01)

(52) U.S. Cl.
CPC .......... *C07C 227/18* (2013.01); *C07C 209/26* (2013.01); *C07D 207/06* (2013.01); *C07D 211/16* (2013.01); *C07D 265/30* (2013.01); *C07C 211/48* (2013.01); *C07C 229/24* (2013.01); *C07C 229/36* (2013.01)

(58) Field of Classification Search
None
See application file for complete search history.

(56) References Cited

U.S. PATENT DOCUMENTS

| | | | |
|---|---|---|---|
| 5,270,464 A | 12/1993 | Kukla et al. | |
| 6,884,887 B1 * | 4/2005 | Riermeier | B01J 31/1875 544/106 |
| 7,230,134 B2 | 6/2007 | Borner et al. | |
| 7,531,697 B2 | 5/2009 | Almena Perea et al. | |
| 7,763,739 B2 | 7/2010 | Kadyrov et al. | |
| 7,834,215 B2 | 11/2010 | Holz et al. | |
| 8,618,328 B2 | 12/2013 | Plenio et al. | |
| 8,816,114 B2 | 8/2014 | Kadyrov et al. | |
| 9,309,344 B2 | 4/2016 | Kadyrov et al. | |
| 9,878,975 B2 | 1/2018 | Kadyrov | |
| 9,890,108 B2 | 2/2018 | Kadyrov | |
| 2007/0213540 A1 | 9/2007 | Perea et al. | |
| 2009/0258883 A1 | 10/2009 | Brion et al. | |

OTHER PUBLICATIONS

International Search Report for corresponding international application PCT/EP2017/051313 filed Jan. 23, 2017.
English language translation of the Written Opinion of the International Searching Authority for corresponding international application PCT/EP2017/051313 filed Jan. 23, 2017.
English language translation of the International Preliminary Report on Patentability for corresponding international application PCT/EP2017/051313 filed Jan. 23, 2017.
Nishimura, Handbook of Heterogeneous Catalytic Hydrogenation for Organic Synthesis, pp. 406-411, John Wiley & Sons, Inc. (2001).
Stein, et al., "Catalytic Hydrogenation of Amides to Amines under Mild Conditions," *Angew. Chem. Int. Ed.* 52(8):2231-2234 (2013).
Swaringen, et al., "Reaction of Ortho Esters with Secondary Amines," *J. Org. Chem.* 45(2):3986-3989 (Sep. 1980).

* cited by examiner

*Primary Examiner* — Kamal A Saeed
(74) *Attorney, Agent, or Firm* — Law Office of: Michael A. Sanzo, LLC

(57) ABSTRACT

The present invention relates to a process for the N-alkylation of amines by reacting an amine with an orthocarboxylic acid ester and with hydrogen in the presence of a hydrogenation catalyst.

20 Claims, No Drawings

REDUCTIVE ALKYLATION OF AMINES WITH ORTHOCARBOXYLIC ACID ESTERS

CROSS REFERENCE TO RELATED APPLICATIONS

The present application is US national stage of international application PCT/EP2017/051313, which had an international filing date of Jan. 23, 2017, and which was published on Aug. 10, 2017. Priority is claimed to European application EP 16154092.7, filed on Feb. 3, 2016.

The present invention relates to a process for the preparation of amines by reductive alkylation of amines or of ammonia by means of orthocarboxylic acid esters in the presence of hydrogen and of a hydrogenation catalyst.

Amines play a dominant role in numerous complex natural substances such as, for example, the alkaloids, vitamins or amino acids, the chemical, pharmaceutical and industrial importance of which is undeniable. As intermediates, amines are used inter alia in the synthesis of pharmaceuticals, agrochemicals, food additives, dyes or cosmetics. For the field of active ingredients, amino acids play a superior role in this regard.

Amines can be prepared inter alia by reduction of the corresponding carboxamides, for example by catalytic hydrogenation of carboxamides (M. Stein and B. Breit, Angew. Chem. Int. Ed. 2013, 52, 2231-2234; WO 2015/067450 A1) or by catalytic hydrogenation of amide acetals, ketene N,O-acetals or ester imides (WO 2015/067448 A1).

A further method, the reductive alkylation of ammonia or of primary or secondary amines by means of aldehydes and ketones, leads in the presence of hydrogen and heterogeneous metal catalysts to an alkylation of the amino group. The reductive alkylation of amines belongs to the most important methods for the preparation of amines (W. S. Emerson, The preparation of amines by reductive alkylation, in Organic Reactions, Vol. 4, 1948, pp. 174-255, Wiley, N.Y.; Catalytic Hydrogenation over Platinum Metals, Academic Press, New York, 1967, p. 291 ff; Catalytic Hydrogenation in Organic Synthesis, Academic Press, New York, 1979, 165 ff; F. Müller and R. Schröter in Methoden Org. Chem. (Houben-Weyl), 1957, XI/1, p. 602-671; S. Nishimura, Handbook of Heterogeneous Catalytic Hydrogenation for Organic Synthesis 2001, pp. 406-411, Wiley, N.Y.). The reaction of aldehydes or ketones with ammonia or primary or secondary amines in the presence of hydrogen and of heterogeneous catalysts, however, generally requires drastic reaction conditions as regards pressure and temperature. By contrast, Riermeier et al. (WO 01/05741 A1) propose a variant of this reaction using homogeneous metal catalysts, in which more mild reaction conditions can be observed.

The reductive alkylation of amines in the presence of hydrogen with heterogeneous catalysis, however, has further disadvantages. During the synthesis of secondary amines by reaction of primary amines with highly reactive aldehydes, it is generally not possible to stop the reaction at the monoalkylation stage. This often leads to relatively complex product mixtures. Furthermore, the methylation of amines by way of reductive alkylation by means of formaldehyde can generally only take place in aqueous solution, since formaldehyde is obtainable exclusively in aqueous solution (in the form of its hydrate). This presents a greater problem during the reductive methylation of amino acids, since the amino acids readily soluble in water are difficult to isolate from aqueous solution.

It is therefore an object of the present invention to provide a new type of process for the alkylation of amines which does not have the disadvantages, described above, that have arisen hitherto when using aldehydes as alkylating agents.

Surprisingly, it has now been found that amines can be alkylated with orthocarboxylic acid esters in the presence of hydrogen and customary hydrogenation catalysts.

The set object is accordingly achieved by a process for the N-alkylation of amines by reacting an orthocarboxylic acid ester with an amine and with hydrogen in the presence of a hydrogenation catalyst.

The process according to the invention is thus a process for the preparation of secondary or tertiary amines by reacting an orthocarboxylic acid ester with a primary or secondary amine and with hydrogen in the presence of a hydrogenation catalyst. In a similar way, it is also possible to synthesize primary amines by reacting an orthocarboxylic acid ester with ammonia and with hydrogen in the presence of a hydrogenation catalyst.

During the reaction of an orthocarboxylic acid ester with an amine and with hydrogen in the presence of a hydrogenation catalyst according to the present invention, the molar ratio of hydrogenation catalyst to the amine used is in a range from 1:10 to 1:100 000. The hydrogen partial pressure is in a range from 0.1 bar to 200 bar. The temperature is set in a range from 20° C. to 200° C.

It is advantageous to carry out the process according to the invention in the presence of catalytic amounts of an acid.

In the process according to the present invention, it is possible for example to react amines with the general formula (I) with an orthocarboxylic acid ester of the formula (II) to give N-alkylated amines, where

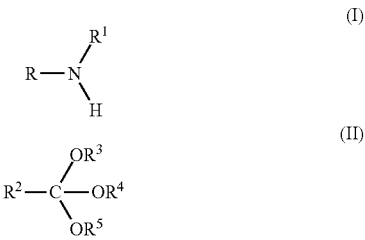

the radicals R and $R^1$ independently of one another are selected from the group consisting of H, or $(C_1\text{-}C_{24})$-alkyl, $(C_3\text{-}C_{20})$-cycloalkyl, $(C_2\text{-}C_{13})$-heterocycloalkyl, $(C_6\text{-}C_{14})$-aryl, or $(C_3\text{-}C_{13})$-heteroaryl radical that is linear or provided with one or more substituents on any desired carbon atom, with the proviso that R and $R^1$ are not simultaneously H, and where the radicals R with $R^1$ can form optionally a saturated or mono- or polyunsaturated $(C_2\text{-}C_{18})$-alkylene or $(C_2\text{-}C_{18})$-heteroalkylene bridge, so that a ring with in total 3-20 ring atoms is formed, and where $R^2$ is selected from the group consisting of H, $(C_1\text{-}C_{24})$-alkyl, $(C_3\text{-}C_{20})$-cycloalkyl, $(C_2\text{-}C_{13})$-heterocycloalkyl, $(C_6\text{-}C_{14})$-aryl, $(C_3\text{-}C_{13})$-heteroaryl and $R^3$, $R^4$ and $R^5$ independently of one another are selected from the group consisting of H, $(C_1\text{-}C_{24})$-alkyl, $(C_3\text{-}C_8)$-cycloalkyl or $(C_6\text{-}C_{14})$-aryl, where both the radicals $R^2$ with $R^3$, as well as $R^3$ with $R^4$ independently of one another can form a saturated or mono- or polyunsaturated $(C_2\text{-}C_{18})$-alkylene or $(C_2\text{-}C_{18})$-heteroalkylene bridge, such that a ring with in total 3-20 ring atoms is formed.

$R^2$ is preferably selected from the group consisting of H, ($C_1$-$C_{24}$)-alkyl, phenyl.

$R^2$ is particularly preferably selected from H, methyl, ethyl, n-propyl, n-butyl, iso-butyl, n-pentyl, n-hexyl, cyclohexyl, n-heptyl, n-octyl, phenyl.

$R^3$, $R^4$ and $R^5$ are preferably selected from the group consisting of methyl, ethyl, n-propyl, iso-propyl, n-butyl, iso-butyl, n-pentyl, n-hexyl, n-heptyl, n-octyl, and phenyl.

A ring is formed preferably between the radicals $R^2$ and $R^3$ or $R^3$ and $R^4$, where the ring is preferably aliphatic and has the alkylene groups propanedi-1,3-yl, butanedi-1,4-yl, pentanedi-1,5-yl or hexanedi-1,6-yl, such that the ring contains in total 4, 5, 6, 7 or 8 ring atoms.

The optional substituents on the radicals R and $R^1$ of the amine of the formula (I) are selected from the group consisting of halogens such as F, Cl, Br, I, and heteroatom-containing functional groups, which contain one or more atoms selected from the group consisting of N, O, P, S, or Si, with single or multiple substitution being possible. Examples of heteroatom-containing functional groups are carbonyl, carboxyl, sulphonate, phosphonate, hydroxyl, amino, ammonium groups such as —OH,
—($C_1$-$C_8$)-alkyloxy
—COOH,
—NH({$C_1$-$C_8$}-acyl),
—NH({$C_1$-$C_8$}-acyloxy)
—N(($C_1$-$C_{20}$)-alkyl)({$C_1$-$C_8$}-acyl),
—N({$C_6$-$C_{14}$}-aryl)({$C_1$-$C_8$}-acyl),
—N({$C_6$-$C_{14}$}-aralkyl)({$C_1$-$C_8$}-acyl),
—N({$C_1$-$C_8$}-acyl)$_2$,
—$NH_3^+$,
—NH({$C_1$-$C_{20}$}-alkyl)$_2^+$,
—NH({$C_6$-$C_{14}$}-aryl)$_2^+$,
—NH({$C_6$-$C_{14}$}-aralkyl)$_2^+$,
—NH({$C_1$-$C_{20}$}-alkyl)({$C_6$-$C_{14}$}-aryl)$^+$,
—N({$C_6$-$C_{14}$}-aryl)({$C_1$-$C_{20}$}-alkyl)$_2^+$,
—N({$C_6$-$C_{14}$}-aryl)$_2$({$C_1$-$C_{20}$}-alkyl)$^+$,
—O—C(=O)—O—{$C_1$-$C_{20}$}-alkyl,
—O—C(=O)—O—{$C_6$-$C_{14}$}-aryl,
—O—C(=O)—O—{$C_6$-$C_{14}$}-aralkyl,
—NH—C(=O)—O—{$C_1$-$C_{20}$}-alkyl,
—NH—C(=O)—O—{$C_6$-$C_{14}$}-aryl,
—NH—C(=O)—O—{$C_6$-$C_{14}$}-aralkyl,
—O—C(=O)—NH—{$C_1$-$C_{20}$}-alkyl,
—O—C(=O)—NH—{$C_6$-$C_{14}$}-aryl,
—O—C(=O)—NH—{$C_6$-$C_{14}$}-aralkyl,
—CN,
—$SO_2$—O—{$C_1$-$C_{20}$}-alkyl,
—$SO_2$—O—{$C_6$-$C_{14}$}-aryl,
—$SO_2$—O—{$C_6$-$C_{14}$}-aralkyl,
—$SO_2$—{$C_1$-$C_{20}$}-alkyl,
—$SO_2$—{$C_6$-$C_{14}$}-aryl,
—$SO_2$—{$C_6$-$C_{14}$}-aralkyl,
—SO—{$C_1$-$C_{20}$}-alkyl,
—SO—{$C_6$-$C_{14}$}-aryl,
—SO—{$C_6$-$C_{14}$}-aralkyl,
—Si({$C_1$-$C_{20}$}-alkyl)$_3$,
—Si({$C_6$-$C_{14}$}-aryl)$_3$,
—Si({$C_6$-$C_{14}$}-aryl)({$C_1$-$C_{20}$}-alkyl)$_2$,
—Si({$C_6$-$C_{14}$}-aryl)$_2$({$C_1$-$C_{20}$}-alkyl),
—{$C_1$-$C_{20}$}-perfluoroalkyl,
—PO(O—{$C_1$-$C_{20}$}-alkyl)$_2$,
—PO(O—{$C_6$-$C_{14}$}-aryl)$_2$,
—PO(O—{$C_1$-$C_{20}$}-alkyl)(O—{$C_6$-$C_{14}$}-aryl),
—PO({$C_1$-$C_{20}$}-alkyl)$_2$,
—PO({$C_6$-$C_{14}$}-aryl)$_2$,
—PO({$C_1$-$C_{20}$}-alkyl)({$C_6$-$C_{14}$}-aryl).

The amine of the general formula (I) is for example an amino acid, for example one of the twenty proteinogenic amino acids or an amino acid derivative, for example an amino acid ester, such as e.g. the methyl or ethyl ester of glycine, alanine, valine, leucine, isoleucine, phenylalanine, aspartic acid, glutamic acid, tryptophan or of proline.

The orthocarboxylic acid ester of the general formula (II) is for example trimethyl orthoformate or triethyl orthoformate, trimethyl orthoacetate or triethyl orthoacetate, trimethyl orthopropanoate or triethyl orthopropanoate, trimethyl orthobutanoate or triethyl orthobutanoate.

Orthocarboxylic acid esters are inexpensive and the preparation methods are well established (H. Lebel, M. Grenon in Science of Synthesis, Vol. 22, 2005, pp. 669-747; G. Simchen in Methoden Org. Chem. (Houben-Weyl), 1985, E5/1, p. 3-192; R. DeWolf, Synthesis, 1974, 153-172). For example, they can be synthesized by alcoholysis of nitriles with alcohols under acid catalysis:

$$R^2CN + 3R^3OH + HCl \rightarrow R^2{-}C(OR^3)_3 + NH_4Cl$$

Orthoformic acid esters can be prepared from chloroform and the sodium alcoholates of the corresponding alcohols (W. E. Kaufmann, E. E. Dreger: Ethylorthoformate [Ethyl orthoformates]. In: Organic Syntheses. 5, 1925, p. 55).

Orthocarboxylic acid esters with different alcohol radicals (R3≠R4≠R5) can be prepared for example by transesterification.

Hydrogenation catalysts selected may be all hydrogenation catalysts contemplated by the person skilled in the art for this purpose.

Preference is given to using heterogeneous hydrogenation catalysts which contain at least one active metal. Preferably, the active metal is one of groups VII B and/or VIII B of the Periodic Table of the Elements, with precious metals and Ni being preferred, and Ru, Rh, Pd, Pt, Re and Ni being particularly preferred. The metals can be present in the hydrogenation catalyst either (a) as such or in the form of metal oxides or (b) as metal complexes.

In case (a), the metal or metal oxide can either be applied to a support or be used as particles. For the support material, there are no limitations. Usually, customary supports such as aluminium oxide, silicon dioxide, aluminium oxide, iron oxide, magnesium oxide, zirconium dioxide, carbon or similar supports known to the person skilled in the field of hydrogenation are used. The content of metal or metal oxide on the support is selected within a range from 1% by weight to 25% by weight, based on the total weight of the catalyst. Preferably, a content of 1% to 5% by weight of metal or metal oxide on the support is selected.

Examples of such hydrogenation catalysts are Pt/C, Pd/C, Ru/C, Rh/C, Pd/CaCO$_3$, Pd/Al$_2$O$_3$, Ru/Al$_2$O$_3$, Rh/Al$_2$O$_3$, Pd/Re/C, Pt/Re/C, RuO$_2$.

In case (b), the metals can also be used in the form of metal complexes as hydrogenation catalysts. Examples thereof are metal complexes of the metals Rh, Ir or Ru, such as e.g. the Wilkinson catalyst ClRh(PPh$_3$)$_3$ or [(dppb)Rh(cod)]BF$_4$, [Ir(PCy$_3$(C$_5$H$_5$N)(cod)]PF$_6$, [Cl$_2$Ru(PPh$_3$)$_3$] and [(dppb)Ru(metallyl)$_2$].

Preferably, the hydrogenation catalyst is selected from the group consisting of Pd/C, Pd/Al$_2$O$_3$, Pd/CaCO$_3$, Pt/C, Ru/Al$_2$O$_3$, Ru/C, Rh/C and [(dppb)Rh(cod)]BF$_4$. Particularly preferably, the hydrogenation catalyst is selected from the group consisting of 5% Pd/C, 5% Pd/Al$_2$O$_3$, 5% Pd/CaCO$_3$, 5% Pt/C, 5% Ru/Al$_2$O$_3$, 5% Ru/C, 5% Rh/C and [(dppb)Rh(cod)]BF$_4$.

The amount of hydrogenation catalyst can be freely selected by the person skilled in the art, where the molar ratio of hydrogenation catalyst to amine is in a range from 1:10 to 1:100 000. Further preference is given to a range from 1:20 to 1:10 000, particular preference being given to a range from 1:50 to 1:2000.

In principle, the person skilled in the art is free to select the solvent that he would like to use in the process according to the invention. On account of the fact that the starting materials are often present in liquid form, it is in this regard also possible to dispense with using a solvent. If, however, the use of solvents in the process according to the invention is desired, it is advantageous to use those solvents which accordingly readily dissolve the components of the reaction used and otherwise have proven to be inert towards the reaction according to the invention. Examples include polar or nonpolar solvents, in particular inter alia hydrocarbons, chlorohydrocarbons, ethers, esters and alcohols. Preference is given here to alkanes, haloalkanes, monohydric and polyhydric alcohols, cyclic and acyclic ethers, and esters.

Preferred solvents are those selected from the group consisting of hexane, heptane, octane, dimethyl glycol ether (DMGE), 1,4-dioxane, methyl tert-butyl ether (MTBE), tetrahydrofuran (THF), ethyl acetate, isopropyl acetate, dibutyl ether, dimethyl carbonate, diethyl carbonate, dipropyl carbonate, methanol, ethanol, isopropanol, butanol, ethylene glycol, dichloromethane and 1,2-dichloroethane. Particular preference is given to methanol and ethanol.

During the reaction, the hydrogen partial pressure of the reaction is established in a range from 0.1 to 200 bar, preferably from 0.1 to 100 bar, and particularly preferably from 0.1 to 60 bar.

The temperature which is to be established during the reaction can be determined by the person skilled in the art and is usually in a range from 0° C. to 250° C. It should be high enough that the envisaged reaction proceeds in a sufficiently rapid time but be as low as possible so that the by-product spectrum during the hydrogenation can be kept as low as possible. Preferably, a temperature in the range from 20° C. to 200° C., preferably in a range from 20° C. to 150° C. is established. Particularly preferably, a temperature in the range from 100° C. to 130° C. is established, and very particularly preferably a temperature in the range from 110° C. to 130° C. is established.

In a particular embodiment of the process according to the invention, the hydrogenation catalyst comprises an active metal.

In a further particular embodiment of the invention, the active metal is a metal of group VII B and/or VIII B of the Periodic Table of the Elements.

In a further particular embodiment of the invention, the reaction furthermore takes place in the presence of an acid. The amount of acid can be freely chosen by the person skilled in the art. However, the acid is preferably used in a molar ratio in a range from 0.01:100 to 10:100, based on the amine.

In principle, the person skilled in the art is free to choose a suitable acid. Preferably, however, cost-effective inorganic or organic acids are used. Preference is given to acids which are selected from the group consisting of mineral acids, carboxylic acids, arylsulphonic acids, alkanesulphonic acids, fluorosulphonic acid. Acids which are selected from the group consisting of p-toluenesulphonic acid (4-MeC$_6$H$_4$SO$_2$OH), CF$_3$SO$_2$OH, CH$_3$SO$_2$OH, CF$_3$COOH, ClCH$_2$COOH, CH$_3$COOH and HCOOH are particularly preferred in this connection.

A particular embodiment of the process according to the invention is that the reaction is carried out in a solvent.

The solvent is preferably selected from the group consisting of hydrocarbons, chlorohydrocarbons, ethers, esters and alcohols.

A further embodiment of the process according to the invention is that the reaction is carried out without solvents.

It is advantageous to work in the absence of water. The invention therefore further provides a process according to the present invention, where anhydrous amine and anhydrous orthocarboxylic acid ester and optionally anhydrous solvent are used.

In the process according to the invention, the procedure generally involves mixing, in an autoclave, the amine, the orthocarboxylic acid ester and the catalyst in a certain molar ratio with a suitable amount of solvent. Then, the autoclave is flushed several times with hydrogen and heated to the reaction temperature and the mixture is hydrogenated at a suitable pressure. After cooling, the hydrogen pressure is let down, the reaction mixture is filtered off and the filtrate is worked up by processes known to the person skilled in the art.

In a preferred embodiment of the process according to the invention, the procedure generally involves mixing, in an autoclave, the amine and the orthocarboxylic acid ester with a suitable amount of solvent and acid. Then, the catalyst is added in a certain molar ratio, the autoclave is flushed several times with hydrogen and the mixture is hydrogenated at a suitable temperature and suitable pressure. After the cooling, the hydrogen pressure is let down, the reaction mixture is filtered off and the filtrate is worked up by a process known to the person skilled in the art.

In a particularly preferred embodiment of the process according to the invention, the procedure generally involves mixing, in an autoclave, the amine and the orthocarboxylic acid ester with a suitable amount of acid. Then, the catalyst is added in a certain molar ratio, the autoclave is flushed several times with hydrogen and the mixture is hydrogenated at a suitable temperature and suitable pressure. After cooling, the hydrogen pressure is let down, the reaction mixture is filtered off and the filtrate is worked up by a process known to the person skilled in the art.

EXAMPLES

General Procedure for the Reductive Alkylation of Amines with Orthocarboxylic Acid Esters An autoclave was filled with catalyst (1 mol % based on the molar amount of amine), flushed with argon and topped up with a solution of amine (0.1 mol) and orthocarboxylic acid ester (0.11-0.3 mol) in 10 ml of methanol (or ethanol) and 0.5 ml of a 0.2 M solution of anhydrous p-toluenesulphonic acid in methanol (or ethanol). The mixture was heated to 120° C. and hydrogen was injected to 40 bar and then the mixture was stirred at a constant pressure until hydrogen absorption could no longer be detected (0.2-6 h). After being filtered off from the catalyst, the filtrate was distilled.

The yields can be found in Table 1.

TABLE 1

Yields in the reductive alkylation of amines with orthocarboxylic acid esters.

| Example No. | Orthocarboxylic acid ester | Amine | Product | Orthocarboxylic acid ester/amine | Hydrogenation catalyst | Time, [h] | Yield [%] |
|---|---|---|---|---|---|---|---|
| 1 | HC(OMe)$_3$ | piperidine | N-methylpiperidine | 2.5 | 3% Pt/C | 3 | 99 |
| 2 | HC(OMe)$_3$ | piperidine | N-methylpiperidine | 2.5 | 5% Ru/Al$_2$O$_3$ | 5 | 98 |
| 3 | HC(OMe)$_3$ | piperidine | N-methylpiperidine | 2.5 | [(dppb)Rh(COD)]BF$_4$ | 6 | 83 |
| 4 | HC(OMe)$_3$ | morpholine | N-methylmorpholine | 2.5 | 5% Pd/C | 1 | 92 |
| 5 | HC(OMe)$_3$ | morpholine | N-methylmorpholine | 2.5 | 5% Pt/C | 0.2 | 97 |
| 6 | HC(OMe)$_3$ | morpholine | N-methylmorpholine | 2.5 | 5% Ru/C | 0.3 | 96 |
| 7 | HC(OMe)$_3$ | morpholine | N-methylmorpholine | 2.5 | 5% Rh/C | 0.3 | 98 |
| 8 | EtC(OMe)$_3$ | PhNH$_2$ | N-propylaniline | 1.1 | 3% Pt/C | 1 | 66 |
| 9 | n-BuC(OEt)$_3$ | pyrrolidine | N-pentylpyrrolidine | 1.3 | 5% Pt/C | 1 | 81 |
| 10 | n-BuC(OEt)$_3$ | pyrrolidine | N-pentylpyrrolidine | 1.3 | 5% Pt/C | 0.2 | 95 |
| 11 | n-BuC(OEt)$_3$ | pyrrolidine | N-pentylpyrrolidine | 1.3 | 5% Ru/C | 0.2 | 90 |
| 12 | n-BuC(OEt)$_3$ | pyrrolidine | N-pentylpyrrolidine | 1.3 | 5% Rh/C | 0.2 | 86 |
| 13 | PhC(OEt)$_3$ | pyrrolidine | N-benzylpyrrolidine | 1.1 | 3% Pt/C | 1 | 93 |
| 14 | PhC(OEt)$_3$ | pyrrolidine | N-benzylpyrrolidine | 1.1 | 5% Rh/C | 1 | 81 |

TABLE 1-continued

Yields in the reductive alkylation of amines with orthocarboxylic acid esters.

| Example No. | Ortho-carboxylic acid ester | Amine | Product | Ortho-carboxylic acid ester/amine | Hydrogenation catalyst | Time, [h] | Yield [%] |
|---|---|---|---|---|---|---|---|
| 15 | HC(OMe)₃ | benzylamine | N,N-dimethylbenzylamine | 3 | 5% Pd/C | 1 | 99 |
| 16 | HC(OMe)₃ | benzylamine | N,N-dimethylbenzylamine | 3 | 5% Pt/C | 0.5 | 99 |
| 17 | EtC(OMe)₃ | alanine ethyl ester | N-propyl alanine ethyl ester | 1.2 | 5% Pd/C | 2 | 64 |
| 18 | EtC(OMe)₃ | alanine ethyl ester | N-propyl alanine ethyl ester | 1.2 | 5% Pt/C | 1 | 69 |
| 19 | EtC(OMe)₃ | leucine ethyl ester | N-propyl leucine ethyl ester | 1.2 | 5% Pd/C | 1 | 82 |
| 20 | EtC(OMe)₃ | leucine ethyl ester | N-propyl leucine ethyl ester | 1.2 | 5% Pt/C | 0.1 | 75 |
| 21 | EtC(OMe)₃ | leucine ethyl ester | N-propyl leucine ethyl ester | 1.2 | 5% Ru/C | 0.5 | 71 |
| 22 | EtC(OMe)₃ | leucine ethyl ester | N-propyl leucine ethyl ester | 1.2 | 5% Rh/C | 0.1 | 85 |
| 23 | EtC(OMe)₃ | phenylalanine ethyl ester | N-propyl phenylalanine ethyl ester | 1.2 | 5% Pt/C | 0.1 | 83 |
| 24 | EtC(OMe)₃ | phenylalanine ethyl ester | N-propyl phenylalanine ethyl ester | 1.2 | 5% Ru/C | 0.2 | 84 |

TABLE 1-continued

Yields in the reductive alkylation of amines with orthocarboxylic acid esters.

| Example No. | Ortho-carboxylic acid ester | Amine | Product | Ortho-carboxylic acid ester/amine | Hydrogenation catalyst | Time, [h] | Yield [%] |
|---|---|---|---|---|---|---|---|
| 25 | EtC(OMe)$_3$ | Ph-CH$_2$-CH(NH$_2$)-C(O)OEt | Ph-CH$_2$-CH(NHPr)-C(O)OEt | 1.2 | 5% Rh/C | 0.2 | 90 |
| 26 | EtC(OMe)$_3$ | EtO-C(O)-CH$_2$-CH$_2$-CH(NH$_2$)-C(O)OEt | EtO-C(O)-CH$_2$-CH$_2$-CH(NHPr)-C(O)OEt | 1.2 | 5% Ru/C | 0.5 | 93 |
| 27 | EtC(OMe)$_3$ | EtO-C(O)-CH$_2$-CH$_2$-CH(NH$_2$)-C(O)OEt | EtO-C(O)-CH$_2$-CH$_2$-CH(NHPr)-C(O)OEt | 1.2 | 5% Rh/C | 0.1 | 95 |
| 28 | HC(OMe)$_3$ | pyrrolidine-2-C(O)OMe (NH) | pyrrolidine-2-C(O)OMe (N-Me) | 3 | 5% Pd/C | 0.5 | 98 |
| 29 | HC(OMe)$_3$ | pyrrolidine-2-C(O)OMe (NH) | pyrrolidine-2-C(O)OMe (N-Me) | 3 | 5% Pt/C | 0.1 | 99 |
| 30 | HC(OMe)$_3$ | pyrrolidine-2-C(O)OMe (NH) | pyrrolidine-2-C(O)OMe (N-Me) | 3 | 5% Ru/C | 0.3 | 98 |
| 31 | HC(OMe)$_3$ | pyrrolidine-2-C(O)OMe (NH) | pyrrolidine-2-C(O)OMe (N-Me) | 3 | 5% Rh/C | 0.3 | 97 |
| 32 | EtC(OMe)$_3$ | pyrrolidine-2-COOH (NH) | pyrrolidine-2-COOH (N-Pr) | 2 | 5% Pt/C | 0.3 | 90 |
| 33 | HC(OEt)$_3$ | piperidine-3-C(O)OEt (NH) | piperidine-3-C(O)OEt (N-Me) | 2 | 5% Pd/C | 0.5 | 82 |

TABLE 1-continued

Yields in the reductive alkylation of amines with orthocarboxylic acid esters.

| Example No. | Orthocarboxylic acid ester | Amine | Product | Orthocarboxylic acid ester/amine | Hydrogenation catalyst | Time, [h] | Yield [%] |
|---|---|---|---|---|---|---|---|
| 34 | HC(OEt)$_3$ | ethyl piperidine-3-carboxylate (NH) | ethyl 1-methylpiperidine-3-carboxylate (NMe) | 2 | 5% Pt/C | 0.2 | 90 |
| 35 | HC(OEt)$_3$ | ethyl piperidine-3-carboxylate (NH) | ethyl 1-methylpiperidine-3-carboxylate (NMe) | 2 | 5% Ru/C | 0.3 | 88 |
| 36 | HC(OEt)$_3$ | ethyl piperidine-3-carboxylate (NH) | ethyl 1-methylpiperidine-3-carboxylate (NMe) | 2 | 5% RhC | 0.3 | 87 |

The invention claimed is:

1. A process for the N-alkylation of amines or of ammonia, comprising reacting an orthocarboxylic acid ester with an amine or with ammonia and with hydrogen in the presence of a hydrogenation catalyst.

2. The process of claim 1, wherein the reaction takes place in the presence of an acid.

3. The process of claim 2, wherein the reaction takes place at a molar ratio of acid to amine in a range from 0.01:100 to 10:100.

4. The process of claim 1, wherein the reaction takes place at a molar ratio of hydrogenation catalyst to the amine used in a range from 1:10 to 1:100 000.

5. The process of claim 1, wherein the reaction takes place at a hydrogen partial pressure in a range from 0.1 bar to 200 bar.

6. The process of claim 1, wherein the reaction is carried out in a temperature range from 20° C. to 200° C.

7. The process of claim 1, wherein the hydrogenation catalyst is a heterogeneous hydrogenation catalyst.

8. The process of claim 7, wherein the heterogeneous hydrogenation catalyst comprises at least one active metal.

9. The process of claim 8, wherein the active metal is a metal of group VII B and/or VIII B of the Periodic Table of the Elements.

10. The process of claim 1, wherein the reaction takes place in a solvent.

11. The process of claim 10, wherein the solvent is selected from the group consisting of hydrocarbons, chlorohydrocarbons, ethers, esters and alcohols.

12. The process of claim 1, wherein the reaction is carried out without solvents.

13. The process of claim 4, wherein the reaction takes place at a hydrogen partial pressure in a range from 0.1 bar to 200 bar.

14. The process of claim 13, wherein the reaction is carried out in a temperature range from 20° C. to 200° C.

15. The process of claim 4, wherein the hydrogenation catalyst is a heterogeneous hydrogenation catalyst.

16. The process of claim 15, wherein the heterogeneous hydrogenation catalyst comprises at least one active metal.

17. The process of claim 16, wherein the active metal is a metal of group VII B and/or VIII B of the Periodic Table of the Elements.

18. The process of claim 17, wherein the reaction takes place in a solvent.

19. The process of claim 18, wherein the solvent is selected from the group consisting of hydrocarbons, chlorohydrocarbons, ethers, esters and alcohols.

20. The process of claim 17, wherein the reaction is carried out without solvents.

* * * * *